United States Patent [19]

Kessler

[11] 4,094,305
[45] June 13, 1978

[54] METHOD AND AN ARRANGEMENT FOR CONTINUOUSLY MEASURING THE PARTIAL PRESSURE OF A GAS IN A SAMPLE

[75] Inventor: Manfred Kessler, Dortmund-Sölde, Germany

[73] Assignee: Max Planck Gesellschaft, Munich, Germany

[21] Appl. No.: 712,248

[22] Filed: Aug. 6, 1976

[30] Foreign Application Priority Data

Apr. 23, 1976 Germany ............................. 2617766

[51] Int. Cl.² ............................................. A61B 5/00
[52] U.S. Cl. .................................. 128/2 E; 128/2 L; 204/195 B
[58] Field of Search ........... 128/2 E, 2 G, 2 L, 2.1 E; 204/195 B, 195 P

[56] References Cited

U.S. PATENT DOCUMENTS

| | | | |
|---|---|---|---|
| 3,926,766 | 12/1975 | Niedrach et al. | 128/2 E X |
| 3,964,470 | 6/1976 | Trombley | 128/2.1 E |
| 3,985,633 | 10/1976 | Lubbers et al. | 128/2 E X |
| 3,998,212 | 12/1976 | Reichenberger | 128/2.1 E X |

Primary Examiner—Robert W. Michell
Assistant Examiner—Michael H. Thaler
Attorney, Agent, or Firm—Michael J. Striker

[57] ABSTRACT

A method and an arrangement for continuously measuring the partial pressure of a gas in a sample, particularly of oxygen dissolved in blood flowing through muscle tissue which is covered by a skin layer, comprises a support probe which is adapted to be positioned intermediate the skin layer and a portion of the sample so that the probe is fixedly held in position against the sample portion. A polarographic cell is mounted on the probe and has a gas-measuring part which is in firm engagement with the sample portion so as to generate a signal indicative of the amount of gas being diffused from the sample portion. The polarographic cell is interchangeably and detachably mounted on the probe so as to facilitate sterilization of the various parts of the arrangement. A plurality of gas-measuring electrodes are utilized in combination with an indicating arrangement to either measure the distribution of the oxygen gas being diffused over an area of the sample portion or to measure the average value of gas being diffused from the latter.

13 Claims, 2 Drawing Figures

METHOD AND AN ARRANGEMENT FOR CONTINUOUSLY MEASURING THE PARTIAL PRESSURE OF A GAS IN A SAMPLE

BACKGROUND OF THE INVENTION

The present invention relates to a method and an arrangement for continuously measuring the partial pressure of a gas in a sample and, more particularly, to such a method and arrangement which measures the partial pressure of oxygen dissolved in blood flowing through muscle tissue which is covered by a skin layer.

The partial pressure measurement of a gas such as oxygen in a sample of living tissue has recently become of growing medical significance. Recent technical developments have made it feasible to measure the amount of oxygen contained in the blood stream which actually flows to the cells of living tissue, i.e. at the end of the respiration chain, rather than relying on the standard technique of measuring the amount of oxygen which actually enters the lungs, i.e. at the beginning point of the respiration chain.

Thus, it is known to measure the partial pressure of oxygen in blood vessels by using a cathetertype device or by using needle or so-called pin electrodes. Such measuring devices are known in the art and reference may be made to Zeitschrift Fuer Kreislaufforschung, 1971, pages 13– 23, or published German application DAS 1,179,393.

It is also known to measure the partial pressure of oxygen in specific cells at specific locations in living tissue by using micro-needle electrodes (Garching Instrumente Prospekt, Naturwissenschaft 1972, page 544).

Furthermore, it is known to measure the partial pressure of oxygen by using polarographic-type devices which are placed on the outer skin layer of living tissue and are operative to receive and measure the amount of oxygen which diffuses through the skin layer. Such devices are also known in the art and reference may be made in this connection to published German applications DOS 2,145,400 or DOS 2,255,879.

However, these prior-art techniques have not proven altogether satisfactory in obtaining measurement data to directly analyze the status of utilization of oxygen of the body by the oxygen partial pressure of its tissue. Recent experiments (Mikrozirkulation Workshop, April 1974, Volume 5, page 36 ff.) indicate that the partial pressure of oxygen in living tissue is very much lower than in the blood vessels. This shows (publication of Max Planck Gesellschaft, 1974, pages 444–463)that the blood is used by the organism as a very large and very readily available butter supply of oxygen. The relatively large concentration gradient of oxygen between the blood vessels and the surrounding tissue is employed by the living organism for the adaptation of the microcirculation to the oxygen partial pressue as needed in the tissue. The ability to change the microcirculation is different to the various organs of the body. Especially the tissue of the skeleton muscles has a high range of adaptation of the microflow to the need for oxygen of the tissue, and the muscle tissue shows large changes in oxygen partial pressure related to the status of oxygen utilization of the body. Reference can be had to Microvascular Research, Volume 8, 1974/283.

It is desirable to accurately measure the partial pressure of oxygen flowing in the blood stream of skeletal muscle tissue. This is particularly true in case of impending hypoxia, wherein the flow of oxygen quickly varies from moment to moment.

SUMMARY OF THE INVENTION

Accordingly, it is a general object of the present invention to overcome the disadvantages of the prior art.

Another object of the invention is to accurately measure the partial pressure of a gas such as oxygen in a sample, such as muscle tissue covered by a skin layer.

An additional object of the present invention is to provide a universally applicable arrangement for measuring the partial pressure of a gas such as oxygen which is compact in construction and simple in manufacture.

Still a further object of the invention is to provide a reliable method for accurately measuring the partial pressure of gas in a sample.

In keeping with these objects and others which will become apparent hereinafter one feature of the invention, briefly stated, is embodied in a method and an arrangement for continuously measuring the partial pressure of a gas in a sample, particularly of oxygen dissolved in blood flowing through a muscle tissue which is covered by a skin layer, which comprises a support probe having first and second probe sections which are adapted to be positioned intermediate the skin layer and a portion of the sample so that the probe is fixedly held in position against the sample portion. The support probe is so positioned by incising the skin layer and inserting the probe through the incision. Furthermore, a polarographic cell is mounted, preferably in an interchangeable and detachable manner, at one of the probe sections and has a gas-measuring part which is positioned so as to be in firm engagement with the sample portion to be measured. The cell has electrodes which are in electrolytic contact with each other so as to generate a signal which is indicative of the amount of gas being diffused from the sample portion.

In accordance with the invention, the gas-measuring polarographic cell at the lower end region of the support 2 which is placed in contact with the sample to be measured will cooperate with sensitive indicating devices and thereby strongly indicate to a user, even small changes in the transport rate of oxygen flowing in the blood stream. This information is especially useful in obtaining a quick and early recognition of the moment of danger for a patient, thus making possible the quick introduction of appropriate medical countermeasures.

In accordance with another feature of the invention, the polarographic cell is interchangeable and detachably mounted at the lower end region of the support probe. This feature assures efficient maintenance for purposes of sterilization and/or the replacement of nonoperative parts.

Furthermore, the support probe has a tapered configuration so that its wall surfaces are placed in sealing engagement with the underside of the outer skin layer and the upper surface of the sample to be measured. This feature permits the polarographic cell which is mounted on the probe to be firmly held in position on the sample, thus leading to a substanial reduction of measurement errors caused by undesirable shifting of the position of the polarographic cell on the sample.

In accordance with yet another feature of the invention, the polarographic cell comprises a plurality of gas-measuring sensor electrodes which are operative for measuring the distribution of the oxygen pressure measurements over an entire surface region of the sample. Each oxygen pressure measurement can be seperately indicated by a respective indicating device.

Alternatively, each partial pressure measurement of oxygen can be combined in a noiseless summing amplifier so as to indicate the total mean value of oxygen in the sample portion.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENT

Figure 1:
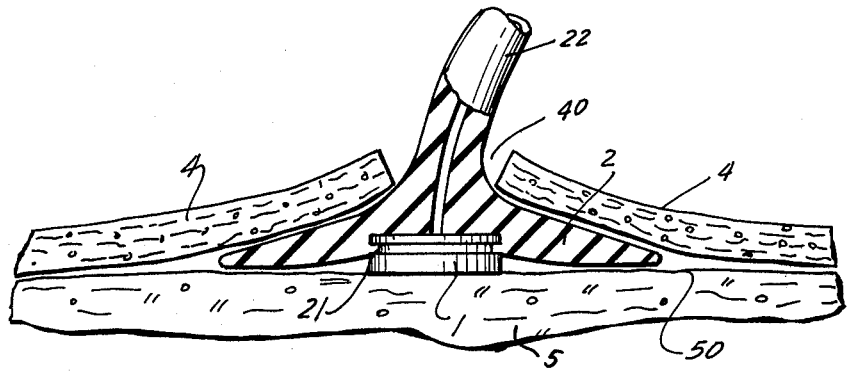
FIG. 1 is a diagrammatic view, partially in section, of a currently preferred embodiment according to the invention.

Referring jointly to the method and arrangement for continuously measuring the partial pressure of a gas in a sample as illustrated in the drawing, it will be seen that reference numeral 5 generally identifies a sample which contains the gas whose partial pressure is to be measured. The sample is muscle tissue which is covered by an exterior skin layer 4.

As shown in FIG. 1 an incision 40 preferably only a few millimeters wide is formed in the skin 4. A probe 2 is thereupon inserted through the incision 40 so that one contact surface of the probe 2 engages the underside of the skin layer 4, and so that another contact surface of the probe 2 engages upper surface 50 of the muscle tissue 5. These tapered surfaces of the probe serve to fixedly hold the probe 2 in position against the muscle tissue 5 and in sealing engagement with the latter and with the skin layer 4.

Figure 2:
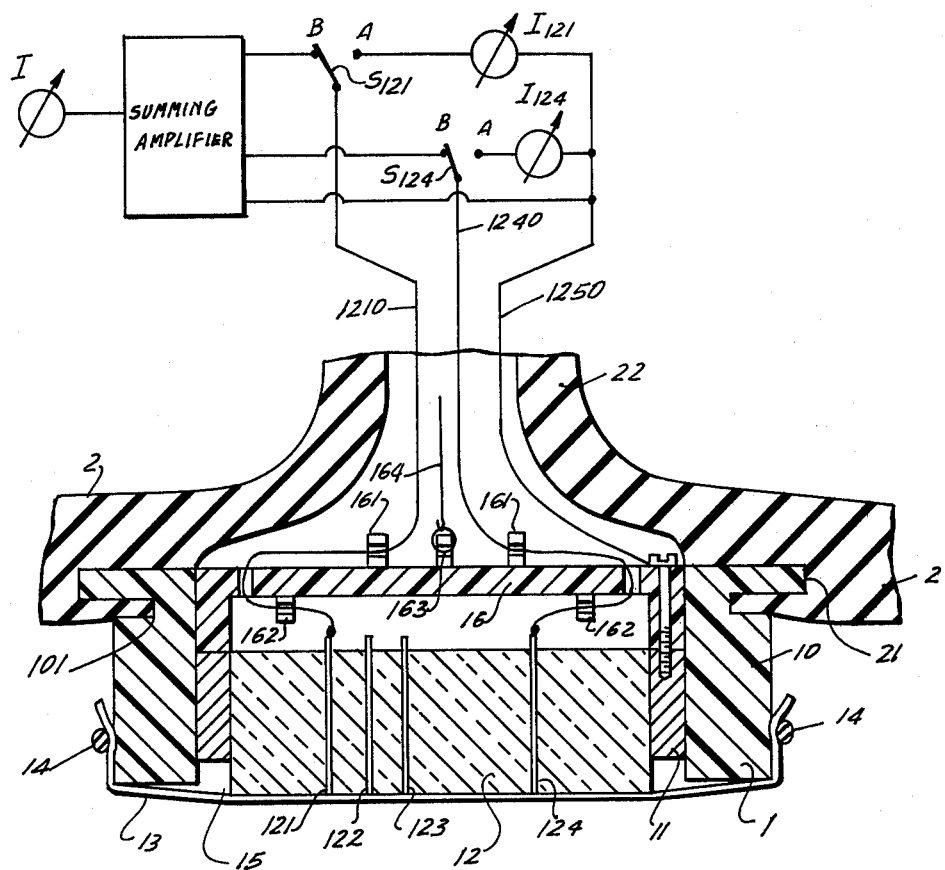
FIG. 2 is an enlarged sectional view of a detail of FIG. 1, and diagrammatically illustrating the electronic processing of the signal generated in accordance with the invention.

At the other contact of the probe 2, i.e. the surface which faces and engages the muscle tissue 5, a polarographic cell 1 is mounted on the probe 2. As shown in the enlarged view of FIG. 2, the polarographic cell comprises at least one and preferably a plurality of gas-measuring sensor electrodes or so-called polarized electrodes 121, 122, 123 ... 124 (only four sensor electrodes being shown for the sake of clarity), each sensor electrode having a cross-sectional diameter of at least 10 microns and at most 20 microns. The sensor electrodes are all spaced from each other in electrically-insulating relationship and are embedded within a glass carrier 12. The sensor electrodes are generally constituted of platinum metal material.

An annular reference or so-called non-polarized electrode 11 is constituted of metal material, and preferably silver chloride coated silver material. Reference electrode 11 surrounds the lass carrier 12.

An annular casing or housing 10 preferably constituted of synthetic plastic material surrounds the reference electrode 11. At the periphery of the upper end region of housing 10, a flange part is formed which is adapted to be interchangeably and detachably lodged in recess 21 formed in the support probe 2.

The housing 10 is also formed with a groove 101 adjacent the flange part so as to receive a corresponding projection of the support probe 2. By virtue of the yieldable nature of the synthetic plastic material casing and of the support probe 2 which is preferably constituted of elastic, silicon rubber, the polarographic cell 1 is securely held in position on the probe 2.

The polarographic cell 1 also comprises a space 15 in which the electrolyte (not illustrated for the sake of clarity), preferably potassium chloride and water, is contained. A gas-permeable membrane 13 overlies space 15 and prevents the electrolyte from escaping from the polarographic cell 1 by sealing means 14, preferably an elastic O-ring seal.

A cover 16, preferably constituted of synthetic plastic material or teflon material is centrally and inwardly located with respect to the housing 10 and overlies the reference electrode and the glass carrier 12 which contains the sensor electrodes 121 - 124. The cover 16 is interchangeably and detachably mounted to the polarographic cell 1 by means of the illustrated screw.

In operation, the reference electrode 11 and at least one of the sensor electrodes react in the presence of the electrolyte with the oxygen gas which is being diffused from the sample portion 5 and through the gas-permeable membrane 13. An electrical signal is thereby generated which is indicative of the partial pressure of oxygen in the sample. The signal is thereupon conducted to the illustrated indicating devices by means of electrial conductors or wires 1210 ... 1250 (only electrical wires 1210, 1240 and 1250 have been illustrated for the sake of clarity). However, it will be understood that additional electrical wires can be electrically connected to other sensor electrodes, such as electrodes 122 and 123.

In order to relieve any possible stress on the illustrated electrical wires 1210 and 1240, stress-reducing lugs 161 and 162 are mounted on or are integral with the cover 16. Upper stress-relief lugs 161 and lower lugs 162 are formed with passages which cooperate with additional passages formed in the cover 16 so as to guide the respective electrical wires in a path towards the interior passage of the flexible tubular section 22 of the support probe 2. The lugs 161 and 162 may be formed of any suitable material, such as synthetic plastic material or of teflon strands. The flexible tubular section 22 is only partially shown in the drawing and essentially protects and maintains the electrical wires in place during the positioning of the polarographic cell on the sample portion.

The indicating devices are arranged at the other end of the elongated tubular section 22, i.e. the end which faces away from the polarographic cell 1. As diagrammatically illustrated in FIG. 2, the indicating devices are connected in two seperate modes depending upon the position of the switches $S_{121}$ and $S_{124}$. If these switches are in position A, then the respective signals generated by electrodes 121 and 124, for example, are respectively conducted via wires 1210 and 1240 to indicating devices $I_{121}$ and $I_{124}$. Conductive wire 1250 completes the electrical circuit. In this position of the switches, the distribution of the partial pressure measurement of oxygen as measured over an area of the sample portion is obtained simply by observing the reading of the various indicating devices $I_{121}$ and $I_{124}$. It will be understood that more than the two illustrated indicating devices $I_{121}$ and $I_{124}$ can also be employed.

Alternatively, if the switches are placed in position B, then the respective electrical signals are conducted via wires 1210 and 1240 to the summing amplifier, wherein the respective signals are combined in any desired manner. For example, the respective signals can be combined so that a single average or mean value of all of the respective electrical signals is indicated on indicating device I.

A further feature of the invention is the provision of a stress-reducing lug 163 which is centrally located at the upper surface of cover 16. A thread 164, preferably of nylon material, is attached to lug 163 to relieve of possible stress to the wires 1210, 1240, 1250.

Thus, in accordance with the invention, the polarographic cell is easy to mount and dismount from the resilient and elastic support probe 2. By constituting the probe 2 of silicon rubber material, the probe is relatively simple to disinfect after each use. It is further desirable to configurate the probe in an annular, disk-shaped configuration or in a substantially circular configuration having a cross-sectional diameter of at least 20 and at most 35 mm. Using these dimensions for the probe, it is desirable to also shape the polarographic cell 1 to have an annular configuration which has a diameter of at least 10 and at most 15 mm. Of course, it will be understood that other configurations are also possible for the probe and the polarographic cell.

It will be understood that each of the elements described above, or two or more together, may also find a useful application in other types of constructions differing from the types described above.

While the invention has been illustrated and described as embodied in a method and an arrangement for continuously measuring the partial pressure of a gas in a sample, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new desired to be protected by Letters Patent is set forth in the appended claims:

1. An arrangement for continuously measuring the partial pressure of oxygen dissolved in blood flowing through muscle tissue which is covered by a skin layer, a combination comprising a support probe having first and second sides which are respectively adapted to engage the underside of the skin layer and the surface of the muscle tissue so that said probe is fixedly held in position against the muscle tissue; and a polarographic cell mounted at said second side and having a gas-measuring part adapted to firmly engage said muscle tissue so as to generate a signal indicative of the amount of gas being diffused from said muscle tissue, said probe further including a tubular section connected to said first side thereof, said first side of said probe comprising tapered wall surface portions which diverge in direction from said tubular section towards said muscle tissue so that said tapered wall surface portions are adapted to be positioned in sealing engagement with the underside of said skin layer.

2. An arrangement as defined in claim 1; and further comprising means for interchangeably and detachably mounting said cell on said probe, comprising a recess formed in said second side, and a flange part provided on said cell, said flange part being lodged in said recess.

3. An arrangement as defined in claim 1, wherein said gas-measuring part of said cell comprises an electrolyte, a reference electrode and a sensor electrode in electrolytic contact with said reference electrode; and further comprising means for indicating the amount of gas diffused from said muscle tissue in dependence upon the value of said generated signal; and further comprising conductive means for conveying said signal in direction away from said electrodes and towards said indicating means.

4. An arrangement as defined in claim 3, wherein said conductive means comprises conductors electrically connected between said electrodes and said indicating means; and a tubular section having an internal elongated passage in which said conductors are received.

5. An arrangement as defined in claim 4, wherein said cell further comprises a detachable cover; and further comprising means for relieving the stress of said conductors, comprising stress-relief members each mounted on said covers and having a support which supports a different part of a respective conductor.

6. An arrangement as defined in claim 1, wherein said probe at said second side has a generally disk-shaped configuration.

7. An arrangement as defined in claim 1, wherein said second side has a generally circular configuration which has a diameter which is at least 20 mm and at most 35 mm.

8. An arrangement as defined in claim 1, wherein said gas-measuring part of said cell comprises a plurality of rod-shaped sensor electrodes, each having a cross-sectional diameter of between 10 microns and 20 microns.

9. An arrangement as defined in claim 1; and further comprising means for measuring the distribution of the gas being diffused over an area of said muscle tissue, said measuring means comprising a plurality of sensor electrodes arranged in said cell at spaced locations therein, each sensor electrode being operative to generate a signal component at a respective one of said locations; and further comprising means for individually indicating a respective one of said signal components generated at each of said locations, said indicating means comprising a plurality of indicating devices each connected with a respective one of said sensor electrodes.

10. An arrangement as defined in claim 1; and further comprising means for measuring the mean amount of gas bring diffused from said muscle tissue, said measuring means comprising a plurality of sensor electrodes arranged in said cell at spaced locations therein, each sensor electrode being operative to generate a signal component at a respective one of said locations; and further comprising means for combining all of said signal components so as to obtain a mean value for the gas being diffused at each one of said locations; and further comprising means for indicating said mean value.

11. A method of continuously polarographically measuring the partial pressure of gas in a sample, particularly of oxygen dissolved in blood flowing through muscle tissue which is covered by a skin layer, the method comprising the steps of incising the skin layer so as to form an incision; inserting through the incision a probe on one side of which is mounted a polarographic cell, engaging the surface of the muscle with said one side of said probe and said polarographic cell mounted thereon, and engaging the underside of the skin layer with the other side of said probe; and with the underside of said skin layer engaged by said other side of said probe, and with said one side of said probe and the polarographic cell mounted thereon both engaging said surface of the muscle tissue, using the polarographic cell to generate a signal indicative of the amount of gas being diffused from said surface of the muscle tissue.

12. The method as defined in claim 11; and further comprising the step of measuring the distribution of the gas being diffused over an area of said surface, said measuring step including the step of using a plurality of gas-measuring sensor electrodes at spaced locations in said cell, each sensor electrode generating a signal component at a respective one of said locations, and the step of seperately indicating a respective one of said signal components generated at each of said locations.

13. The method as defined in claim 11; and further comprising the step of measuring the mean amount of gas being diffused from said surface, said measuring step including the step of using a plurality of gas-measuring sensor electrodes of spaced locations in said cell, each sensor electrode generating a signal component at a respective one of said locations, and combining all of said signal components so as to obtain a mean value for the gas being diffused at each one of said locations, and indicating said mean value.

* * * * *